US00PP35671P2

(12) United States Plant Patent
Wheeler et al.

(10) Patent No.: US PP35,671 P2
(45) Date of Patent: Mar. 5, 2024

(54) BLUEBERRY PLANT NAMED "BB14-112PT-2"

(50) Latin Name: *Vaccinium corymbosum*
Varietal Denomination: BB14-112PT-2

(71) Applicant: BB IP Repository, LLC, Grand Junction, MI (US)

(72) Inventors: Edmund J. Wheeler, Holland, MI (US); Maria Pilar Banados, Santiago (CL)

(73) Assignee: BB IP Repository LLC, Grand Junction, MI (US)

( * ) Notice: Subject to any disclaimer, the term of this patent is extended or adjusted under 35 U.S.C. 154(b) by 0 days.

(21) Appl. No.: 18/217,303

(22) Filed: Jun. 30, 2023

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Karen M Redden
(74) *Attorney, Agent, or Firm* — King IP Law; Joshua King

(57) ABSTRACT

'BB14-112PT-2', is another genotype selected in a tropical environment of Peru. 'BB14-112PT-2' does not require chill-hours for either budbreak or fruit production. The fruit of 'BB14-112PT-2' is large to extra-large size berry, with medium blue color, good fruit firmness texture. Leaves are large and shoots has short internodes. The eating quality of 'BB14-112PT-2' is very good and superior to many of the varieties currently grown in Peru, with a sugar/acid balance of 12 to 15. Time of fruit production in 'BB14-112PT-2' can be regulated by the pruning date and environment conditions.

8 Drawing Sheets

Figure 1A:
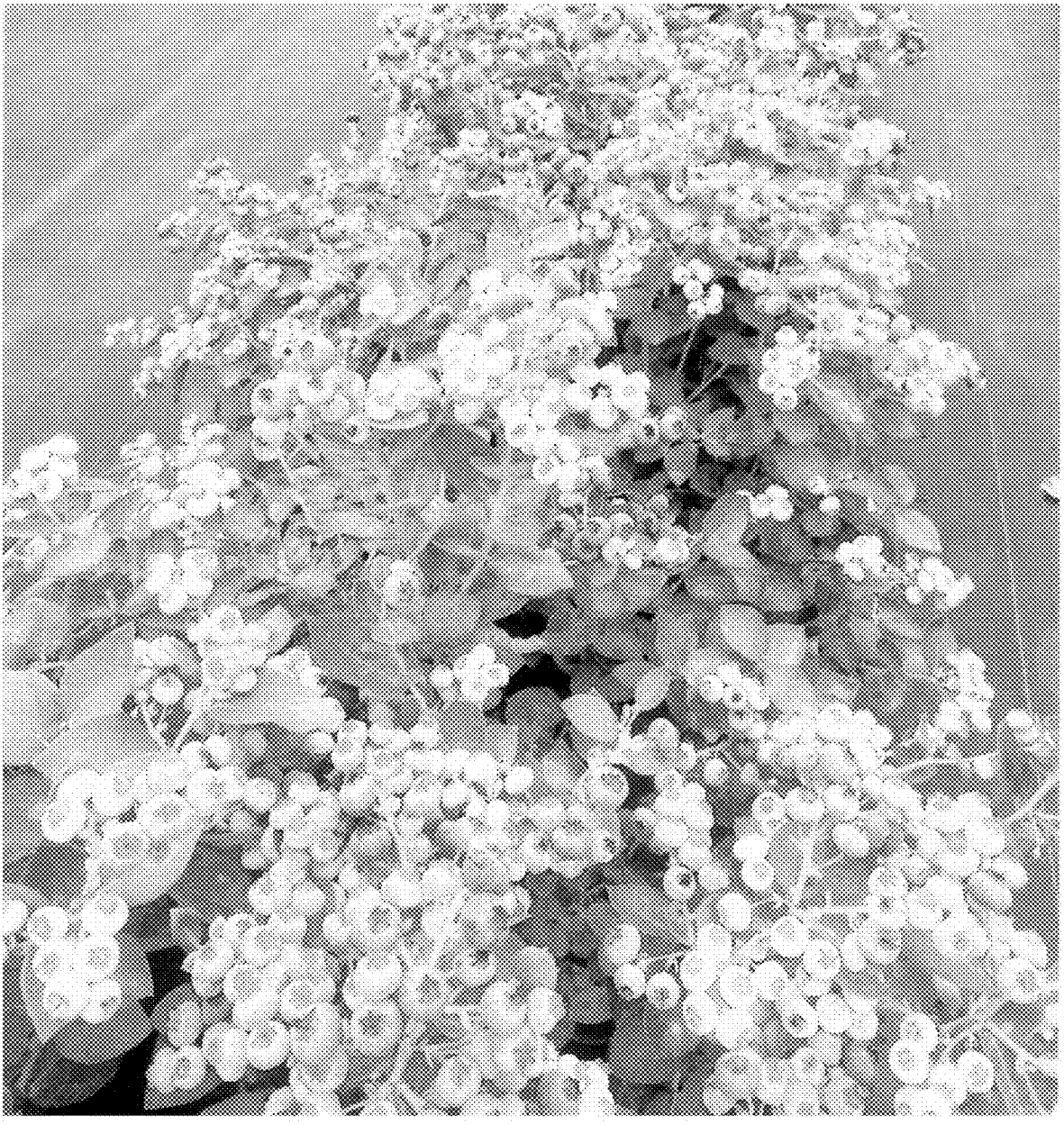

Latin Name: *Vaccinium corymbosum.*
Common name: Blueberry.
Cultivar name: 'BB14-112PT-2'.

BACKGROUND AND SUMMARY

Blueberries are a well-known fruit enjoyed by many throughout the world. The novel blueberry variety in this application, 'BB14-112PT-2', is a new genotype from selected in the tropical environment of Chao, Peru.

One example of an existing known blueberry variety in the same environment is 'Ventura', U.S. Plant Pat. No. 24,606. Compared to 'Ventura', 'BB14-112PT-2' is a smaller plant and has lower vigor, and is more precocious. The fruit of 'BB14-112PT-2' is large and is located on the apical portion of vertical current-season shoots and is well presented on the plant and is produced in current season shoots rather than in 1-year-old shoots, which is another feature of 'BB14-112PT-2', similar to 'BB15-214PO-3'. The fruit of 'BB14-112PT-2' is sweet, with medium acidity and a very pleasant flavor, large size and very early.

Comparing 'BB14-112PT-2' to 'Stellar' (brand name for "BB06-50FL-1", U.S. Plant Pat. No. 30,445); the fruit of 'BB14-112PT-2' is similar in size, it has a darker blue color, has less persistent bloom (wax that cover the fruit) and more flat shape; and the fruiting wood of 'BB14-112PT-2' is current season-shoots rather than in one-year-old shoots.

Additional examples of an existing, patented blueberry variety is 'Rocio', U.S. Plant Pat. No. 20,374, and 'Emerald', U.S. Plant Pat. No. 12,165. Compared with these varieties in Peru, the acidity of 'BB14-112PT-2' is lower than them as shown in Table 1, which provides fruit characteristics of 'BB14-112PT-2' compared to several other commercial varieties grown in Peru.

TABLE 1

Fruit characteristics of several blueberry varieties grown in Chao, Peru compared to BB12-

| Cultivar | Fruit size (g) | Firmness Baxlo (shore) | Sugar Content (°brix) | Acidity (%) | Ratio °Brix/ Acidity |
|---|---|---|---|---|---|
| Ventura | 2.3 | 79 | 11.2 | 1.15 | 10.1 |
| Rocío | 3.2 | 78 | 12.2 | 1.00 | 12.0 |
| Emerald | 2.1 | 75 | 10.1 | 1.20 | 8.4 |
| BB14-112PT-2 | 3.7 | 73 | 12.6 | 0.96 | 13.1 |

112PT-2. Data is average of several samples of fruit taken during harvest season 2021-2022.

The present cultivar, 'BB14-112PT-2', provides one or more advantages compared to these and/or other blueberry varieties.

The fruit of 'BB14-112PT-2' is blue color, with good firmness. The eating quality of 'BB14-112PT-2' is very good, having a sugar/acidity balance of 13.1 higher than other commercial cultivars in Peru like Ventura, Rocio or Emerald. 'BB14-112PT-2' is a highly productive variety with very early maturity fruit and very good fresh market quality. Time of fruit production in 'BB14-112PT-2' can be regulated by the pruning date and moderated by the environment conditions in the tropical environment of Peru. This is another distinct characteristic of 'BB14-112PT-2', particularly in this new tropical environment for blueberries. 'BB14-112PT-2' does not require chill-hours for either budbreak or fruit production, which appears to be because 'BB14-112PT-2' does not develop endo-dormancy. 'BB14-112PT-2' was selected in sandy soil in Chao, Peru and tested under soil and substrate soilless production in Perú and in Chile.

Areas of adaptation of 'BB14-112PT-2' include coast of Peru, Ecuador, and Colombia and other tropical and subtropical areas with no winter chill conditions. 'BB14-112PT-2' was also tested in the temperate area of the Central Valley in Chile.

Plants of 'BB14-112PT-2' are medium upright with a medium size crown 'BB14-112PT-2' produces several semi-upright canes, with reddish shoot colors and with good leafing and flowering. Leaf are large in size.

The fruit of 'BB14-112PT-2' is moderate sweet with medium acid, have a large and firm berry adapted to a tropical non-chill environment as well as temperate low-chill environment. The berry scar of "BB14-112PT-2' is medium and dry. 'BB14-112PT-2' shows a long fruit storability of about 3 weeks. The productivity of 'BB14-112PT-2' is higher than 'BB15-214PO-3' and similar to 'Rocio' in Peru, although it has yet not been tested commercially.

The flowering period of 'BB14-112PT-2' is extended and can last 3 to 4 months and is similar to 'Rocio' in the same tropical environment of Peru. Flowering of 'BB14-112PT-2' starts 50 to 60 days after pruning, which is shorter than 'Scintilla' (U.S. Plant Pat. No. 19,233) and 'Ventura', which take about 120 to 150 days. The fruiting period of 'BB14-112PT-2' is similar to 'Kestrel' (brand name for FL02-40, U.S. Plant Pat. No. 21,719) starting about 120 to 130 days after pruning and lasting for 5 to 6 months. Ripening of 'BB14-112PT-2' is extended and it is presented in two or three flushes of harvest in current season shoots.

BRIEF DESCRIPTION OF THE PHOTOGRAPHS

Figure 1B:
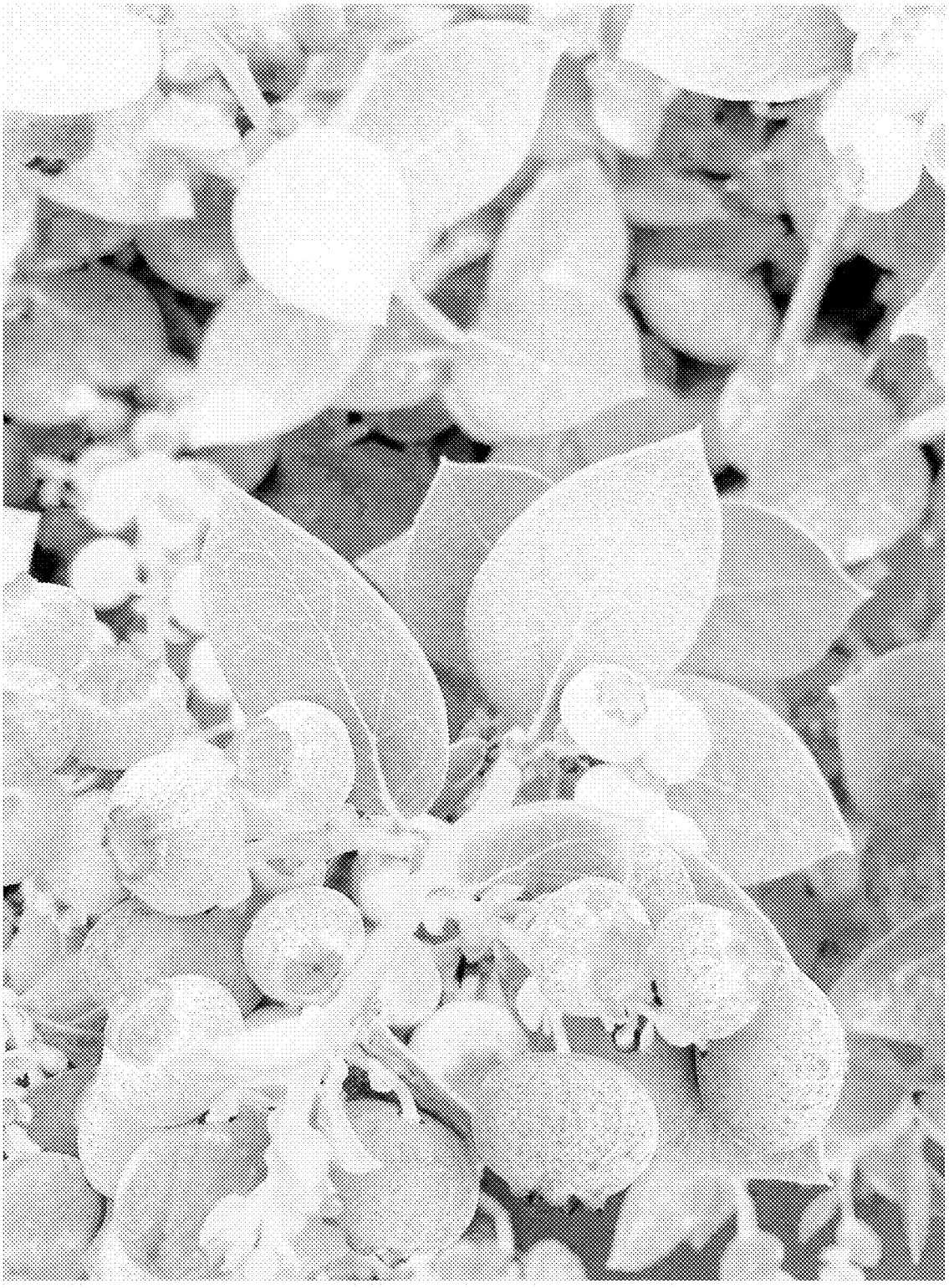
Figure 1C:
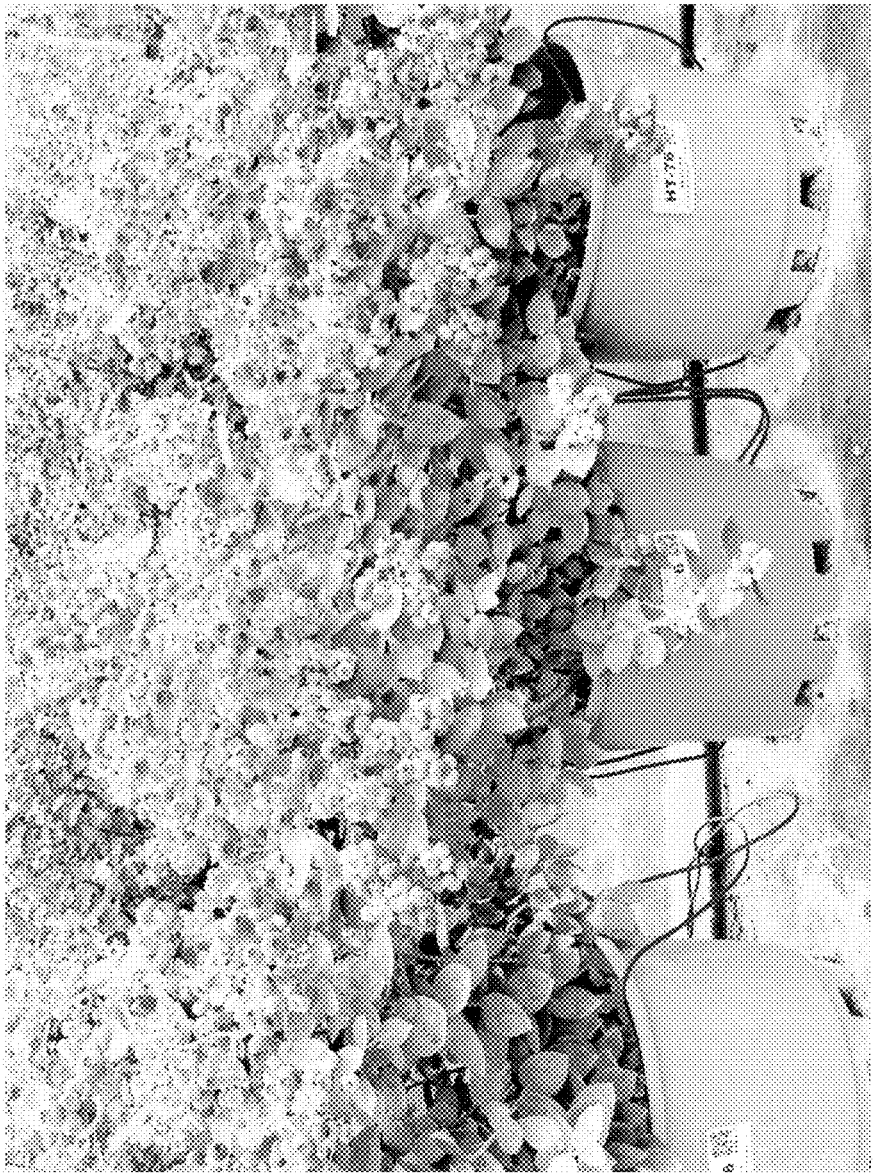
Figure 2A:
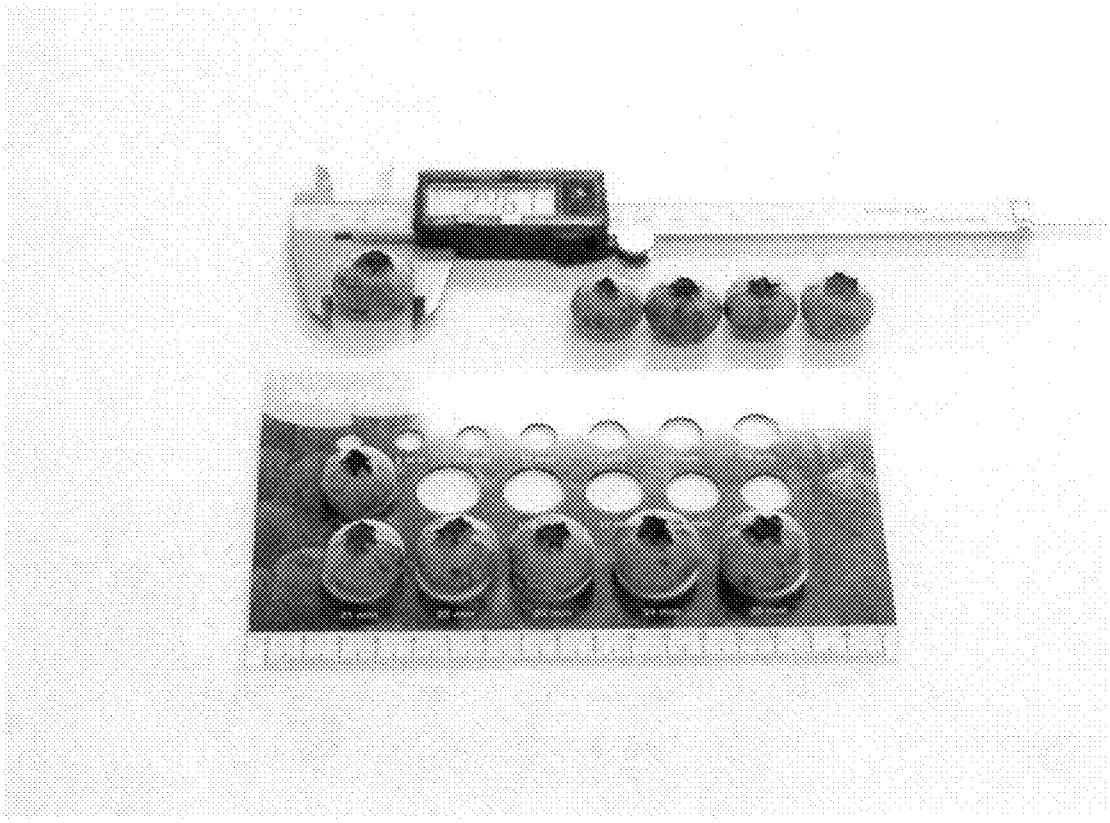
Figure 2B:
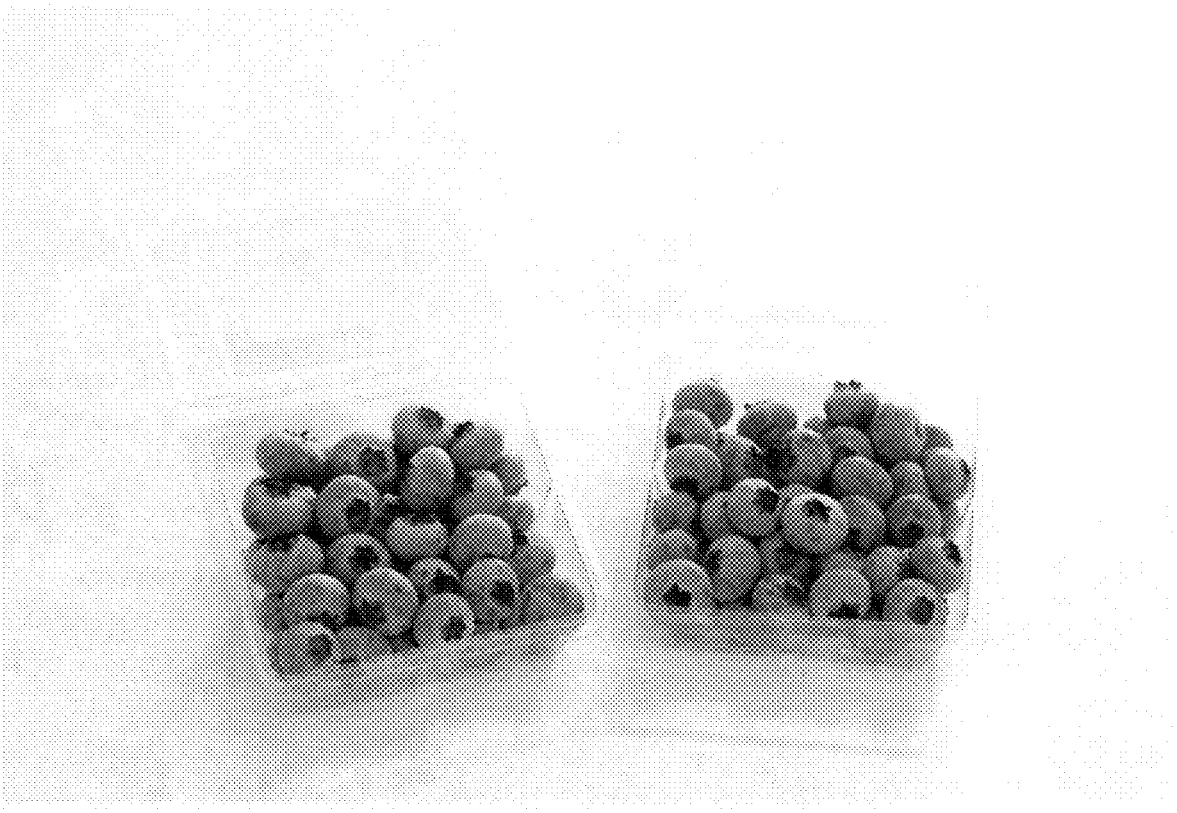

FIGS. 1A-1C are close-up photographs of showing one of the clonal 2-years-old plants of 'BB14-112PT-2' in Chao, Peru, and showing the abundant fruit in the abundant plant. (1B) is a picture of the productive plant with a cluster of fruit and leaves margins. (1C) is a picture of a clonal plant of BB14-112PT-2 grown in soilless system in Chao Peru taken in July 22, showing the plant habit, leaf shape and abundant fruit on different maturity stages FIGS. 2A and 2B are close-up photographs of fruit taken in Chao, Peru, (2A) size of fruits (2B) clamshells of fruits of 'BB14-112PT-2'

Figure 3A:
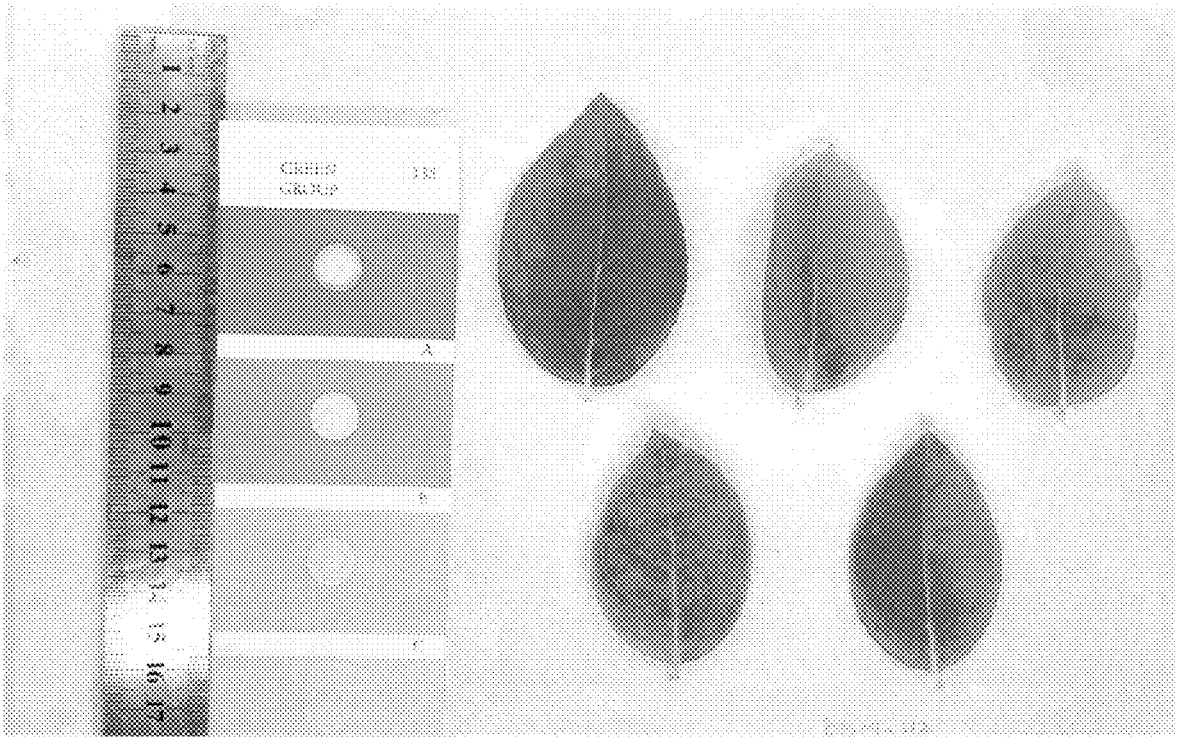
Figure 3B:
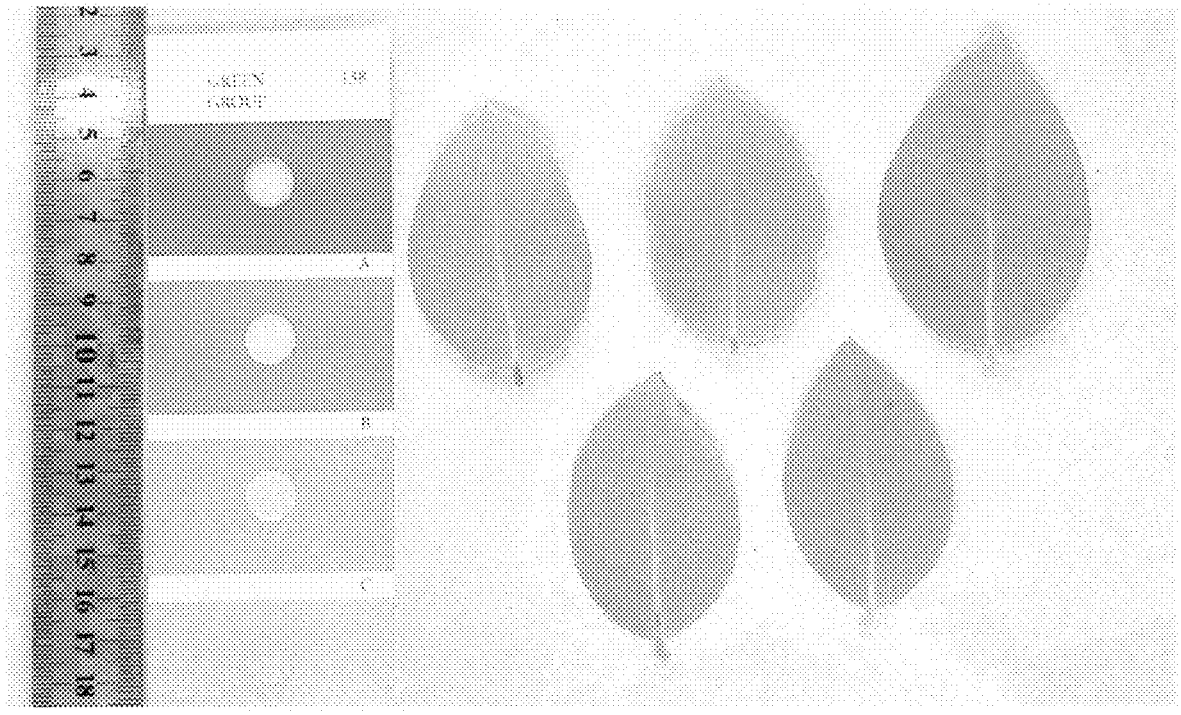
Figure 4:
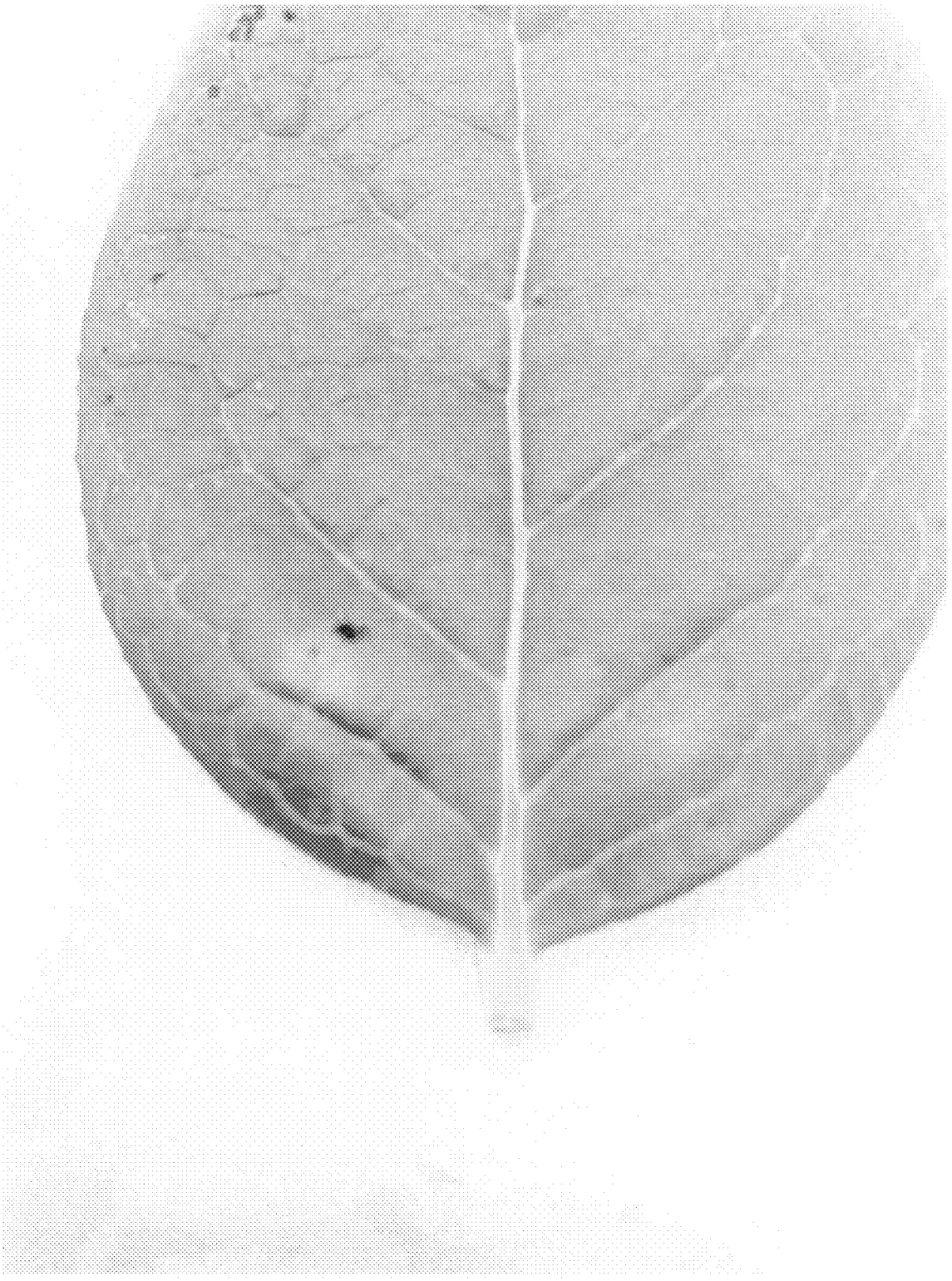

FIGS. 3A, 3B are photographs of 'BB14-112PT-2' leaves showing the size of the leaves and color for both leaves 'sides FIG. 4 is a photograph of 'BB14-112PT-2' leaf petiole

DETAILED DESCRIPTION

Note: statements of characteristics herein represent exemplary observations of the cultivar performance in Chao, Peru 8°35'12"S 78°35'58"W and will vary depending on time of year, location, annual temperature conditions and weather, etc. Where dimensions, sizes, colors, and other characteristics are given, it is to be understood that such characteristics are approximations and averages. The descriptions reported herein are based on the original selected individual bush observed in successive years through 2018, 2019, 2020 and 2021 in fields near Chao, Peru and also in cloned plants planted in Chao, Peru in 2019 and 2020. Laboratory analysis of fruit characteristics were done in Chao, Peru.

Cultivar Name: 'BB14-112PT-2'

Classification:

Family: Ericaceae.

Botanical name: *Vaccinium corymbosum*

Common name: Blueberry.

Parentage:

FEMALE PARENT

Name: 'Emerald' (child of, FL91 69 (unpatented) xNC1528 (unpatented)).

U.S. Plant Pat. No. 12,165

Compared to 'Emerald', 'BB14-112PT-2' is earlier, sweeter and less acidic, has larger fruit size and firmer berries on the same environment of Chao, Peru.

MALE PARENT

Name: 'Sapphire' (parents unknown).

U.S. Plant Pat. No. 11,829

Compared to 'Sapphire', fruit of 'BB14-112PT-2' is larger, firmer, and less aromatic, and produce fruit on current season shoots.

'BB14-112PT-2' originated as a seedling selected from a cross of 'Emerald' and 'Sapphire' made in a greenhouse in Grand Junction, Michigan in 2014. Seed was germinated in Chile and plants of that cross were grown and then sent and planted in a seedling evaluation site in Chao, Province of La Libertad, Peru in Feb 2016. The plant was first selected in September 2016 based on its excellent fruit characteristics both in the field and after 5 days cold storage and was given the number 'BB14-112PT-2'. It was tested under this number for three years. The individual bush was observed and evaluated for productivity and fruit quality in the same site for three successive years from 2016 through 2018. An additional 40 bushes were propagated by in vitro and planted in an advanced trial in a soil and in soilless system near Chao, Peru in July 2019 and the fruit was evaluated in 2020 and 2021. All the observed bushes have retained the characteristics of the original selection.

'BB14-112PT-2' has been asexually propagated via tissue-cultured micro shoots since 2018. Propagated plants have been under evaluation in Chao, Peru since July 2019.

General description of 'BB14-112PT-2'

'BB14-112PT-2' is a new and distinct non-chill tetraploid Southern/Tropical highbush blueberry variety (*Vaccinium*) of complex ancestry, based largely on *V. corymbosum* and *V. darrowii*. 'BB14-112PT-2' is a very productive early-season variety of short cycle from pruning to harvest similar to 'BB14-112PT-2', with high quality fresh market characteristics 'BB14-112PT-2' is particularly well suited to be cultivated in tropical areas. 'BB14-112PT-2' has a semi-upright bush and a large sized crown with many new vertical canes. The bush has a medium vigor and is very productive. It has shown very good adaptability to sandy soil and substrate mix of coco fiber and peat in Peru. The fruit itself is medium blue color, with firm texture. The eating quality is excellent with a higher sugar/acidity balance than 'Emerald', 'Ventura' and 'Rocio' in Peru. Fruit should be picked on a regular schedule about 7 days to maintain the quality of the fruit. 'BB14-112PT-2' will be released an improvement over 'Emerald', 'Rocio' and 'Ventura' in terms of flavor and overall eating experience.

References to color refer to The Royal Horticultural Society Colour Chart 2007 Fifth Edition.

Morphological characteristics reference: Plant Systematics, Jones and Luchsinger, 2 Ed., McGraw Hill, New York, ISBN 0-07-032796-3, 1986.

Device used to measure Soluble Solids)(SS-Brix°), Titratable acidity (TA), pH: PAL-BX/Acid 7, Atago USA, Inc., Bellevue, WA.

Firmness readings: Shore by BAXLO Durometer (Chao, Peru)

General Description: medium upright with a large size crown and medium vigor; sweet, medium acid, firm berry adapted to a tropical non-chill environment 'BB14-112PT-2' blooms about 50 to 60 days after pruning. The average 50% ripening date is 180 days after pruning. Firmness ranges from 70 to 75 Baxlo Shore, Brix° from 12 to 13% and titratable acidity from 0.75 to 0.95% and sugar to acid ratio of 12 to 20. Storability is medium and it could last up to 20 days in cold storage.

Specific features of the variety:

Plant:

*Growth habit.*—Semi-upright.
*Plant width.*—75 cm at mid-bush height.
*Plant height.*—74 cm.
*Productivity.*—2.5 to 3.0 kg per plant.
*Cold hardiness/tolerance.*—Not tested.
*Chilling requirement.*—This is a tropical highbush and this plant does not require chill hours for bud break.
*Canes.*—Moderately branched, average 4 to 6 shoots per bush, average 40-70 cm length, medium number of laterals.
*Young current-season-shoots.*—Green Group 141 D.
*One-year-old shoot branches color.*—Yellow-Green Group 145A. Texture is soft.
*Mature cane color.*—Grey Brown 199-A.
*Mature Cane texture.*—Rough.
*Fruiting wood.*—Current season shoots.
*Internode length range.*—1.5 to 2 cm.
*Surface texture of new wood.*—Smooth.
*Time of beginning of leaf bud burst.*—Bud break occurs 8 to 10 days after pruning in Chao, Peru.
*Time of beginning of flowering.*—50 to 60 days after planting or pruning in Chao, Peru.
*Date of* 50% open flowers.—70 to 80 days after planting or pruning in Chao, Peru for the first flush of flowers.
*Time of beginning of fruit ripening.*—Fruit ripening begins on 120 to 130 days after planting or pruning.
*Disease resistance/susceptibility.*—None claimed.
*Young current-season-shoots.*—Green Group 141D.
*One-year-old short branches color.*—Green Group 138 C.

Foliage:

*Young, newly expanded leaf color.*—Upper surface: green gray 143-B, lower surface: green 138-B.
*Leaf arrangement.*—Simple Alternate.
*Mature, fully expanded leaves.*—Upper surface: green group138-A, lower surface: green group 138-B.
*Leaf margins.*—Slightly serrate.
*Leaf venation.*—Pinnate.
*Leaf Shape.*—Ovate.
*Leaf length.*—65 to 87 mm, average 72 mm.
*Leaf width.*—53 to 58 mm, average 55 mm.
*Leaf color.*—Green group 138-A.
*Leaf apices.*—Acuminate.
*Leaf bases.*—Acute.
*Vein and petiole coloration.*—Color vein: Yellow green 154-A.
*Color petiole.*—Yellow green 145-B.
*Petiole length.*—2.7 to 4.4 mm, average 3.6 mm.
*Petiole diameter.*—1.5 mm.
*Evergreen.*—'BB14-112PT-2' is evergreen and keep its leaves during the entire year.
*Fall leaf color.*—Does not apply for this genotype since it keeps the leaves year round as green leaves.

Leaf dimensions:

*Overall shape.*—Ovate.
*Leaf length.*—65 to 87 mm, average 72 mm.
*Leaf width.*—53 to 58 mm, average 55 mm.
*Leaf margins.*—Slightly serrate, no visible (microscope 10×) pubescence and a few nectaries Leaf surface: Smooth upper and lower, no visible (microscope 10×) pubescence.

Leaf buds:

*Shape.*—Medium obtuse.
*Length.*—1.8 mm.
*Width.*—1.4 mm.
*Color.*—Yellow green group 145-C with some greyed orange group 172-C.

Flower buds:

*Shape.*—Round.
*Length.*—4.5 mm.
*Width.*—3.7 mm.
*Color.*—Greyed-orange 175-B.

Flower:

*Flower shape.*—Globose.
*Number per lateral.*—14 to 18.
*Flowers per cluster.*—4 to 8.
*Flower fragrance.*—Light floral.
*Corolla color.*—White 155-C.
*Corolla length.*—6.2 mm.
*Corolla width.*—10.2 mm.
*Corolla aperture width.*—4.2 mm.
*Corolla texture.*—Smooth.
*Flower peduncle length.*—5.6 mm.
*Peduncle diameter.*—1.6 mm.
*Peduncle texture.*—Smooth.
*Peduncle color.*—Yellow green N144-C.
*Flower pedicel length.*—3.4 mm.
*Pedicel diameter.*—0.8 mm.
*Pedicel texture.*—Smooth.
*Pedicel color.*—Green gray142-C.
*Calyx* (*with sepals*).—3.1 mm.
*Calyx color.*—Green gray 141-C.
*Stamen length.*—5 to 6 mm.
*Stamen number per flower.*—10.
*Stamen filament color.*—Greyed-green 193-B.
*Style.*—8 mm, top of ovary to stigma tip.
*Style color.*—Green N 144-C.
*Pistil extends over the top of corolla.*—1 mm.
*Ovary color.*—Green 147-B.
*Anther length.*—4.3 mm.
*Number.*—1.
*Anther color.*—Greyed-orange N172-C.

Pollen:

*Abundance.*—Medium high.
*Color.*—Yellow 8-D.

Fruit: Date of 50% maturity: 120 to 130 days after pruning.

*Duration of ripening.*—Average 65 to 80 days from bloom to ripen in Chao, Peru and Ripening period can last 6 months.
*Yield.*—3 kg per plant.
*Cluster density.*—Medium.
*Immature fruit color.*—Green 130-D.
*Berry color with wax.*—Violet Blue 98-D.
*Berry color with wax removed.*—Blue 103-A.
*Berry flesh color.*—Green 138-D.
*Berry surface wax abundance.*—Persistent.
*Berry weight.*—Average 3.5 to 4.2 grams/berry.
*Berry size diameter.*—20.6 mm.
*Berry height.*—15 mm.
*Berry width.*—18 to 22 mm.
*Aspect* (*H/W*).—0.65 Berry.
*Shape.*—Oblate.

*Average number of fruits per cluster.*—4 to 8.

*Detachment force.*—Easy.

*Self-fruitfulness.*—Fair, cross pollination may be desirable for maximum yield and fruit size.

*Fruit stem scar.*—2 mm diameter, 1 mm depth.

*Calyx.*—5 lobed.

*Calyx diameter.*—11 mm.

*Calyx depth.*—0.3 mm.

*Berry firmness.*—Firm, 75 to 78 Shore of Baxlo.

*Berry sweetness.*—High, Brix°=12 to 14.

*Berry acidity.*—Titratable acidity=0.7% to 0.9%.

*Berry flavor and texture.*—Good blueberry flavor, balanced sugar and acidity, and firm texture.

*Storage ability.*—Medium 3 to 4 weeks in refrigerated storage.

*Suitability for mechanical harvesting.*—Not tested.

Seed:

*Seed abundance in fruit.*—Abundant 18 to 25 seed per fruit.

*Seed color.*—Pantone Greyed-orange group 177A.

*Seed dry weight.*—8 mg.

*Seed size.*—0.4 mm length, 0.4 mm width.

Possible typical market uses: Mainly fresh market. It can also be used for processing and/or as frozen fruit.

What is claimed is:

1. A new tropical highbush blueberry plant cultivar named 'BB14-112PT-2' as described and shown herein.

* * * * *